United States Patent [19]

O'Lenick, Jr. et al.

[11] 4,336,386
[45] Jun. 22, 1982

[54] QUATERNARY IMIDAZOLINIUM PHOSPHITE DERIVATIVES

[75] Inventors: Anthony J. O'Lenick, Jr., Fairlawn; Raymond L. Mayhew, Summit, both of N.J.

[73] Assignee: Mona Industries, Inc., Paterson, N.J.

[21] Appl. No.: 159,409

[22] Filed: Jun. 13, 1980

Related U.S. Application Data

[62] Division of Ser. No. 965,457, Nov. 30, 1978, Pat. No. 4,243,602.

[51] Int. Cl.³ .................................................. C07F 9/65
[52] U.S. Cl. ...................... 548/112; 548/119; 544/157; 544/243
[58] Field of Search ................ 548/112, 119; 544/157, 544/243

[56] References Cited

U.S. PATENT DOCUMENTS 2,713,583  7/1955  Smith ................................. 252/357
3,304,349  2/1967  Shen .................................. 260/945
3,686,368  8/1972  Eiseman .............................. 260/945
3,856,893 12/1974  Diery et al. ......................... 548/112
4,215,064  7/1980  Lindemann et al. ................. 548/112

FOREIGN PATENT DOCUMENTS 2132290 11/1972  France .
  45-573   9/1970  Japan .
 276408  10/1970  U.S.S.R. .

Primary Examiner—John M. Ford
Assistant Examiner—Natalia Harkaway
Attorney, Agent, or Firm—Felfe & Lynch

[57] ABSTRACT

Novel quaternary compounds of the formula

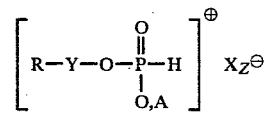

wherein

R is a tertiary amine radical of from 6 to 40 carbon atoms;

Y is alkylene, optionally interrupted by up to 3 oxygen atoms, of up to 12 carbon atoms, optionally containing a substituent selected from lower alkyl, alkoxy, hydroxy or hydroxyalkyl of not more than 10 carbon atoms each;

A is selected from OM or OYR$^+$ wherein Y and R are defined as above and

M is an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or a salt radical selected from alkali metals, alkaline earth metals and mono-, di-, or tri-ethanolamine;

$X^-$ is an anion;

Z is an integer from 1 to 2, with the proviso that when A is OM, Z is 1 and when A is OYR, Z is 2.

2 Claims, No Drawings

QUATERNARY IMIDAZOLINIUM PHOSPHITE DERIVATIVES

This is a division of application Ser. No. 965,457, filed Nov. 30, 1978, now U.S. Pat. No. 4,243,602 issued Jan. 6, 1981.

THE INVENTION

The novel quaternary compounds of the invention may be represented by the following general formula:

$$\left[ R^{\oplus}-Y-O-\overset{O}{\underset{A}{\overset{\|}{P}}}-H \right]_z (X^{\ominus}) \quad (I)$$

wherein
A is selected from OM or OYR+
X− is an anion
z is an integer from 0 to 2
with the proviso that z is of a value necessary for charge balance (i.e., when A is OM, z is 1, when A is O—Y—R+, z is 2).

R is an amidoamine reactant moiety of the formula:

$$\left[ R^1-\overset{O}{\overset{\|}{C}}-\overset{R^2}{\underset{}{N}}-(CH_2)_n-\overset{R^3}{\underset{R^4}{N}} \right]^{\oplus}$$

wherein
$R^1$ is alkyl, alkenyl, alkoxy, or hydroxyalkyl of from 5 to 22 carbon atoms each, or aryl or alkaryl of up to 20 carbon atoms,
$R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms,
$R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, e.g., a morpholino structure, in which the Y radical is bonded to a ring atom of said N-heterocycle other than the nitrogen of the R moiety;
n is an integer from 2 to 12

The term "polyoxyalkene radical" as used above in the definition of $R^2$, $R^3$ and $R^4$ may be of the formula $(R^5-O-R^{5'})_{m'}$ wherein $R^5$ and $R^{5'}$ are alkyl of from 1 to 4 carbon atoms and m' is an integer from about 2 to 10.

In addition to the foregoing definitions wherein R is amidoamine, R may be an N-heterocyclic radical which may contain one additional hetero atom (e.g., oxygen sulfur nitrogen) and contains 5 to 6 total ring carbon atoms; optionally said heterocyclic radical may be substituted with alkyl and/or hydroxyalkyl of up to 20 carbon atoms each. Typical of such N-heterocyclic radicals are imidazolyl, N-alkylmorpholino, alkylpyrimidino, alkyloxazolinyl, and the like. Such compounds may be represented by the formula:

$$\begin{array}{c} R_6 \\ | \\ N-R^1 \\ (CH_2)_o \diagup \diagdown (CH_2)_p \\ \diagdown Z \diagup \end{array}$$

wherein
Z is N, S or O
o is an integer from 0 to 3;
p is an integer from 1 to 3; provided that the sum of o+p is from 3 to 4;
$R^1$ is defined as before and is linked to a ring carbon atom; and
$R^6$ is alkyl of from 2 to 6 carbon atoms which may be substituted with a hydroxyl group at the terminal or a non-terminal carbon atom.

Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each.

M is an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms.

Particularly preferred sub-groups of the compounds of formula can be represented as follows:

$$\left[ R^{\oplus}-Y-O-\overset{O}{\underset{OM}{\overset{\|}{P}}}-H \right] X^{\ominus} \quad (II)$$

$$\left[ R^+-Y-O-\overset{O}{\underset{H}{\overset{\|}{P}}}-OYR^+ \right] 2X^- \quad (III)$$

The compounds of general formula III are bis quaternary containing 2 amine moieties. Compounds III and IV require the presence of an anion (X−) for charge balance. Said X− radical can be anion such as hydroxy or a halide, sulfate, phosphate, or a negatively charged (anion) radical supplied by a solvent or a reactant used in the synthesis of compounds of formulas II' and III. For instance X− may be the halide moiety ("Hal") released in the reactions below.

$$(3) \quad \left[ R-Y-O-\overset{O}{\underset{H}{\overset{\|}{P}}}-OM \right]^{\oplus} X^- \quad (III)$$

$$\uparrow -Hal \qquad (IIIa)$$

$$R + Hal-Y-O-\overset{O}{\underset{H}{\overset{\|}{P}}}-OM$$

wherein R is an amine reactant of the formulas:

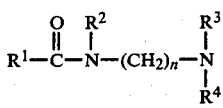

OR

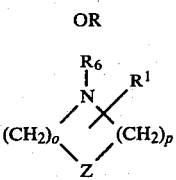

in which the radicals are defined as above.

$$(IV) \quad \left[ R^{\oplus}-Y-O-\underset{H}{\overset{\overset{O}{\|}}{P}}-O-Y-R \right]^{\oplus} 2X^{-}$$

(IVa)

↑ − Hal $$2R + Hal-Y-O-\underset{H}{\overset{\overset{O}{\|}}{P}}-O-YHal$$

wherein the radicals are defined as above.

Preparation of Intermediate "R" Reactants

The amine reactant "R" applicable to all of the syntheses, is, in general, prepared by reacting an acid with an aminoalkyl-substituted tertiary amine to result in the amidoamine function. Alternatively, an acid can be reacted with an aminoalkyl-substituted secondary amine, followed by further treatment of the reaction product with alkylene oxide. Finally, when R represents the N-heterocyclic structure, e.g., imidazolyl, this can be prepared in accordance with known techniques, e.g., as taught in U.S. Pat. No. 2,267,965.

Reaction (4) below yields the non-cyclic reactants "R" and Reaction (5) illustrates the preparation of a typical cyclic amine reactant R (Imidazolyl):

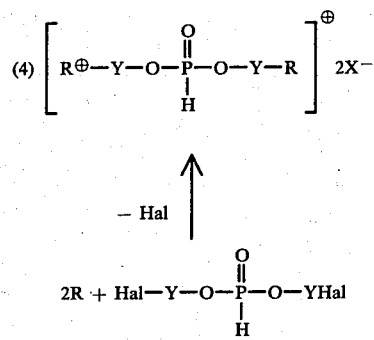

(5) $R^1-C-OH +$

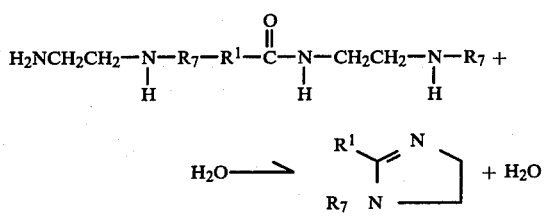

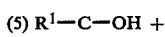

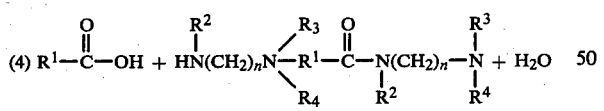

wherein, $R^1$ is defined as above and $R^7$ is alkyl of 2 to 6 carbon atoms which may be substituted with a hydroxyl group (at the terminal or a non-terminal carbon atom. This cyclic reactant can be prepared as disclosed in U.S. Pat. No. 2,267,965.

Preparation of Phosphite Ester Intermediate Reactants

The preparation of the phosphite ester intermediate reactants

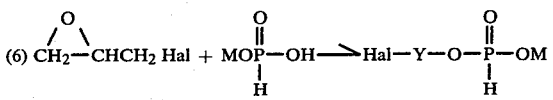

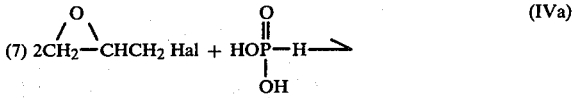

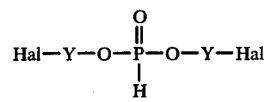

In carrying out the reactions 6 to 7 as set forth above leading to the ultimate quaternary compound of the invention, the amine intermediate reactant (R) is reacted with the appropriate phosphite ester intermediate reactant and these reactions are generally carried out in an aqueous system at 90°–95° C. The quaternary product will have a final pH at 10% of 6–8, depending on the specific nature of the product, i.e., the nature of the amine reactant employed.

These novel quaternary are good surfactants and quite unexpectedly exhibit good foam volume and superior foam stability in comparison to commercially available amphoteric and zwitterionic surfactants.

The compounds of this invention were tested by a "cylinder shake test" for the evaluation of foaming characteristics.

In this test solutions containing 0.1% by weight of the candidate surfactant in water of 100 ppm hardness (calcium to magnesium ratio 3:2) were used and placed in 100 ml stoppered cylinders which had been cleaned so that water drains down its walls in an unbroken film. Each cylinder filled with test solution was shaken twenty (20) times in a standard manner and net foam in ml is noted one minute and again five minutes after shaking. The tests were run in triplicate. The results were as follows:

|  | Example Number | One Minute | Five Minutes |
|---|---|---|---|
| Lauric Myristic Amido Betaine* | — | 67 | 60 |
| Cocoamido Betaine* | — | 70 | 63 |
| Coco Betaine* | — | 65 | 56 |
| Bis(Lauric Myristic Amido Propyl)Phosphitaine | 8 | 86 | 78 |

*Prior art comparison materials Manufactured, e.g., by Mona Industries, Inc. under the tradenames "Monateric LMAB", "Monateric CAB" and "Monateric CB", respectively.

The preparation of specific compounds of the invention is illustrated by the following specific examples. For simplicity, there are first set forth the specific phosphite ester intermediate reactants which were used in the examples, in conjunction with certain tertiary amine reactants which are specifically set forth in each example.

Phosphite Ester Intermediate Reactants

REACTANT "A"

$$ClCH_2-\underset{OH}{\underset{|}{CH}}-CH_2O-\underset{\underset{H}{|}}{\overset{\overset{O}{\|}}{P}}-OCH_2-\underset{OH}{\underset{|}{CH}}-CH_2Cl$$

REACTANT "B"

$$ClCH_2-\underset{OH}{\underset{|}{CH}}-CH_2O-\underset{\underset{H}{|}}{\overset{\overset{O}{\|}}{P}}-OCH_2-\underset{OH}{\underset{|}{CH}}-\underset{OH}{\underset{|}{CH_2}}$$

Phosphite Ester Intermediate Reactant Preparation

REACTANT "A"

$$ClCH_2-\underset{OH}{\underset{|}{CH}}-CH_2O-\underset{\underset{H}{|}}{\overset{\overset{O}{\|}}{P}}-OCH_2-\underset{OH}{\underset{|}{CH}}-CH_2Cl$$

To 60.00 parts of soft water in a suitable reactor, slowly charge 12.28 parts $NaH_2PO_3$ under good agitation. Heat slowly to 40°–45° C. Slowly charge 27.72 parts epichlorohydrin under good agitation. Seal reactor and apply 5 PSIG nitrogen. Heat to 90°–95° C. and hold 3–4 hours. Reaction is complete when there is no acid value.

REACTANT "B"

$$ClCH_2-\underset{OH}{\underset{|}{CH}}-CH_2O-\underset{\underset{H}{|}}{\overset{\overset{O}{\|}}{P}}-OCH_2-\underset{OH}{\underset{|}{CH}}-\underset{OH}{\underset{|}{CH_2}}$$

To 60.00 parts of soft water in a suitable reactor, slowly charge 16.20 parts of $Na_2HPO_3$ under good agitation. Heat to 40°–50° C. Slowly charge 23.79 parts epichlorohydrin under good agitation. Seal reactor and apply 5 PSIG nitrogen. Heat to 90°–95° C. and hold 3–4 hours. Reaction is complete when theoretical reduction in acid value has occurred and inorganic chloride reaches 50% of theoretical.

PRODUCTS

Example #1

$$(R-\overset{\overset{O}{\|}}{C}-\underset{\underset{H}{|}}{N}-(CH_2)_3-\overset{\overset{CH_3}{|}}{\underset{\underset{CH_3}{|}}{\oplus N}}-CH_2-\underset{OH}{\underset{|}{CH}}-CH_2O)_2-\overset{\overset{O}{\|}}{P}-H$$

To 60.00 parts of soft water in a suitable reactor, charge 19.66 parts of Reactant "A" under good agitation. Heat to 45°–50° C. and charge 20.34 parts of 3 cocamido propyl dimethyl amine under good agitation. Heat to 90°–95° C. and hold 4–5 hours. Reaction is complete when theoretical inorganic chloride is generated and when residual tertiary nitrogen levels become vanishingly small.

The product is an aqueous solution of the above material. $R=C_7-C_{17}$

Example #2

$$(R-\overset{\overset{O}{\|}}{C}-\underset{\underset{H}{|}}{N}-(CH_2)_3-\overset{\overset{CH_3}{|}}{\underset{\underset{CH_3}{|}}{\oplus N}}-CH_2-\underset{OH}{\underset{|}{CH}}-CH_2O)_2-\overset{\overset{O}{\|}}{P}-H$$

To 60.00 parts of soft water in a suitable reactor, charge 20.81 parts of Reactant "A" under good agitation. Heat to 45°–50° C. and charge 19.19 parts of 3 lauramido propyl dimethyl amine under good agitation. Heat to 90°–95° C. and hold 4–5 hours. Reaction is complete when theoretical inorganic chloride is generated and when residual tertiary nitrogen levels become vanishingly small.

The product is an aqueous solution of the above material. $R=C_{11}$

Example #3

$$(R-\overset{\overset{O}{\|}}{C}-\underset{\underset{H}{|}}{N}-(CH_2)_3-\overset{\overset{CH_3}{|}}{\underset{\underset{CH_3}{|}}{\oplus N}}-CH_2-\underset{OH}{\underset{|}{CH}}-CH_2O)_2-\overset{\overset{O}{\|}}{P}-H$$

To 60.00 parts of soft water in a suitable reactor, charge 23.10 parts of Reactant "A" under good agitation. Heat to 45°–50° C. and charge 16.90 parts of 3 caprylamido propyl dimethyl amine under good agitation. Heat to 90°–95° C. and hold 4–5 hours. Reaction is complete when theoretical inorganic chloride is generated and when residual tertiary nitrogen levels become vanishingly small.

The product is an aqueous solution of the above material $R=C_7$

Example #4

$$(R-\overset{\overset{O}{\|}}{C}-\underset{\underset{H}{|}}{N}-(CH_2)_3-\overset{\overset{CH_3}{|}}{\underset{\underset{CH_3}{|}}{\oplus N}}-CH_2-\underset{OH}{\underset{|}{CH}}-CH_2O)_2-\overset{\overset{O}{\|}}{P}-H$$

To 60.00 parts of soft water in a suitable reactor, charge 24.44 parts of Reactant "A" under good agitation. Heat to 45°–50° C. and charge 15.56 parts of 3 capramido propyl dimethyl amine under good agitation. Heat to 90°–95° C. and hold 4–5 hours. Reaction is complete when theoretical inorganic chloride is generated and when residual tertiary nitrogen levels become vanishingly small.

The product is an aqueous solution of the above material. $R=C_5$

Example #5

$$\left(\begin{array}{c}\overset{+}{N}-CH_2-\underset{OH}{\underset{|}{CH}}-CH_2O\\ \| \\ \underset{\underset{CH_2CH_2OH}{|}}{N}\diagdown\overset{\overset{}{C}}{\phantom{x}}_R\end{array}\right)_2-\overset{\overset{O}{\|}}{P}-H$$

To 60.00 parts of soft water in a suitable reactor, charge 20.64 parts of Reactant "A" under good agitation. Heat to 45°–50° C. and charge 19.36 parts of 1 hydroxyethyl 2 alkyl 2 imidazoline (alkyl being $C_7$ to $C_{17}$) under good agitation. Heat to 90°–95° C. and hold 4–5 hours. Reaction is complete when theoretical inorganic chloride is generated and when residual tertiary nitrogen levels become vanishingly small.

The product is an aqueous solution of the above material. $R=C_7-C_{17}$

Example #6

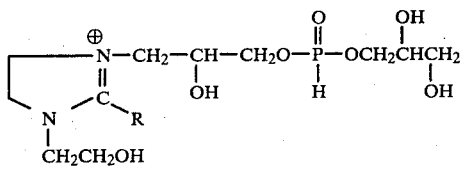

To 60.00 parts of soft water in a suitable reactor, charge 22.14 parts of Reactant "B" under good agitation. Heat to 45°–50° C. and charge 17.86 parts of 1 hydroxyethyl 2 alkyl 2 imidazoline (alkyl being $C_7$ to $C_{17}$) under good agitation. Heat to 90°–95° C. and hold 4–5 hours. Reaction is complete when theoretical inorganic chloride is generated and when residual tertiary nitrogen levels become vanishingly small.

The product is an aqueous solution of the above material. $R=C_7-C_{17}$

Example #7

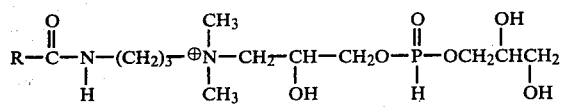

To 60.00 parts of soft water in a suitable reactor, charge 21.12 parts of Reactant "B" under good agitation. Heat to 45°–50° C. and charge 18.88 parts of 3 colamido propyl dimethyl amine under good agitation. Heat to 90°–95° C. and hold 4–5 hours. Reaction is complete when theoretical inorganic chloride is generated and when residual tertiary nitrogen levels become vanishingly small.

The product is an aqueous solution of the above material $R-C_7-C_{17}$

Example #8

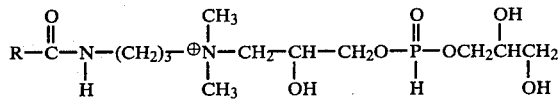

To 60.00 parts of soft water in a suitable reactor, charge 21.5 parts of Reactant "B" under good agitation. Heat to 45°–50° C. and charge 18.5 parts of a 70/30 blend of 3 lauramido propyl dimethyl amine +3 myristamido propyl dimethyl amine under good agitation. Heat to 90°–95° C. and hold 4–5 hours. Reaction is complete when theoretical inorganic chloride is generated and when residual tertiary nitrogen levels become vanishingly small.

The product is an aqueous solution of the above material. $R=70\%-C_{11}/30\%-C_{13}$

Example #9

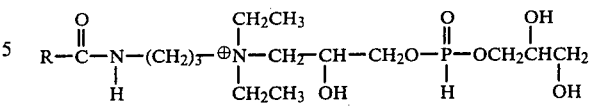

To 60.00 parts of soft water in a suitable reactor, charge 20.29 parts of Reactant "B" under good agitation. Heat to 45°–50° C. and charge 19.71 parts of 3 cocamido propyl diethyl amine under good agitation. Heat to 90°–95° C. and hold 4.14 5 hours. Reaction is complete when theoretical inorganic chloride is generated and when residual tertiary nitrogen levels become vanishingly small.

The product is an aqueous solution of the above material. $R=C_7-C_{17}$

Example #10

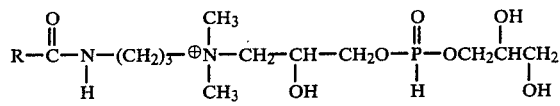

To 60.00 parts of soft water in a suitable reactor, charge 25.28 parts of Reactant "B" under good agitation. Heat to 45°–50° C. and charge 14.72 parts of 3 capramido propyl dimethyl amine under good agitation. Heat to 90°–95° C and hold 4–5 hours. Reaction is complete when theoretical inorganic chloride is generated and when residual tertiary nitrogen levels become vanishingly small.

The product is an aqueous solution of the above material $R=C_5$

Example #11

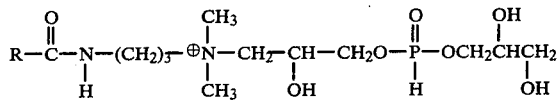

To 60.00 parts of soft water in a suitable reactor, charge 19.62 parts of Reactant "B" under good agitation. Heat to 45°–50° C. and charge 20.38 parts of 3 oleamido propyl dimethyl amine under good agitation. Heat to 90°–95° C. and hold 4–5 hours. Reaction is complete when theoretical inorganic chloride is generated and when residual tertiary nitrogen levels become vanishingly small.

The product is an aqueous solution of the above material. $R=C_{17}$

Example #12

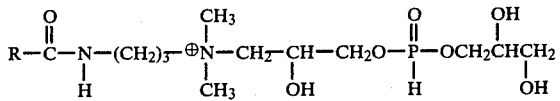

To 60.00 parts of soft water in a suitable reactor, charge 22.30 parts of Reactant "B" under good agitation. Heat to 45°–50° C. and charge 17.70 parts of 3 lauramido propyl dimethyl amine under good agitation. Heat to 90°–95° C. and hold 4–5 hours. Reaction is complete when theoretical inorganic chloride is generated and when residual tertiary nitrogen levels become vanishingly small.

The product is an aqueous solution of the above material. $R=C_7-C_{17}$

Example #13

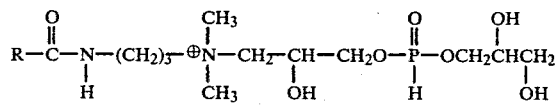

To 60.00 parts of soft water in a suitable reactor, charge 24.54 parts of Reactant "B" under good agitation. Heat to 45°–50° C. and charge 15.46 parts of 3 caprylamido propyl dimethyl amine under good agitation. Heat to 90°–95° C. and hold 4–5 hours. Reaction is complete when theoretical inorganic chloride is generated and when residual tertiary nitrogen levels become vanishingly small.

The product is an aqueous solution of the above material. $R=C_7$

What is claimed is:

1. Quaternary compound of the formula

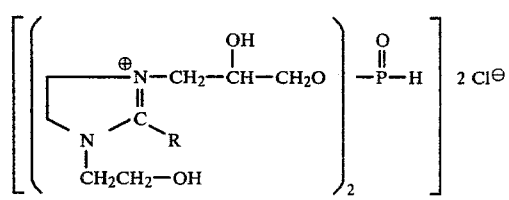

wherein R is alkyl of 7 to 17 carbon atoms.

2. Quaternary compound of the formula

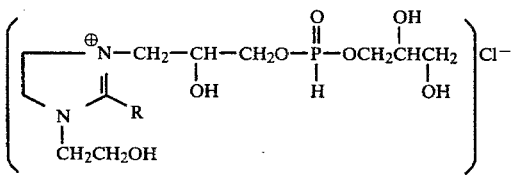

wherein R is alkyl of 7 to 17 carbon atoms.

* * * * *